(12) United States Patent
Myrman et al.

(10) Patent No.: US 6,360,744 B1
(45) Date of Patent: Mar. 26, 2002

(54) USER INTERFACE

(75) Inventors: Mattias Myrman, Stockholm (SE); Michael Strehl, Pfreimd; Herbert Grässl, Schwandorf, both of (DE)

(73) Assignee: Microdrug AG, Hergiswil NW (CH)

( * ) Notice: Subject to any disclaimer, the term of this patent is extended or adjusted under 35 U.S.C. 154(b) by 0 days.

(21) Appl. No.: 09/686,085

(22) Filed: Oct. 12, 2000

(30) Foreign Application Priority Data

Sep. 25, 2000 (SE) .............................................. 0003412

(51) Int. Cl.$^7$ ............................................ A61M 15/00
(52) U.S. Cl. .............................. 128/203.15; 128/200.23
(58) Field of Search ..................... 128/203.15, 203.12, 128/200.14, 200.23, 200.11, 200.16, 205.23; 116/311–315, 318, 319, 308, 307

(56) References Cited

U.S. PATENT DOCUMENTS

| | | | | |
|---|---|---|---|---|
| 5,469,750 A | * | 11/1995 | Llyod et al. ............. | 73/861.61 |
| 5,522,378 A | * | 6/1996 | Ritson et al. .......... | 128/200.14 |
| 5,743,252 A | * | 4/1998 | Rubsamen et al. .... | 128/200.14 |
| 5,755,218 A | * | 5/1998 | Johansson et al. ..... | 128/200.14 |

* cited by examiner

Primary Examiner—John G. Weiss
Assistant Examiner—Teena Mitchell
(74) Attorney, Agent, or Firm—Young & Thompson (57) ABSTRACT

An interface arrangement is disclosed for ensuring proper dosing as well as achieving a safe operation and handling of a dry powder inhaler (DPI) used for administration of a powder to be inhaled. The interface of the present invention primarily handles the loading of a cassette (4) carrying pre-metered doses into the dry powder inhaler (8). An important characteristic is that the interface by utilizing a particular coding prevents a user from loading a cassette not containing the proper powder. Additionally the interface informs a user when a new mouthpiece has to be replaced after being used for a pre-defined number of inhalation operations. Additionally the interface informs a user when a present cassette has delivered its last dose and should be exchanged. Also information on the number of further cassettes already utilized will control that another cassette still is permitted to be loaded. If this counter exceeds a pre-defined number of used cassettes the inhaler then is by definition worn out, whereby the present dry powder inhaler has to be scrapped. In that case the last cassette will not be able to be released from the inhaler device but will accompany the inhaler when it is discarded.

7 Claims, 10 Drawing Sheets

Inhalation of the first dose

| Action | Dose counter indicator 18c | Dose counter indicator 18b |
|---|---|---|
| 1. Insert cassette | ⇌ | ☐ |
| 2. Open device | ⇌ | ☐ |
| 3. Close device – Ready for inhalation | ☐ | 7 |
| 4. Open device | ☐ | 7 |
| 5. Inhale | 6 | ☐ |
| 6. Close device | ☐ | 6 |

Fig. 7

Inhalation of the last dose

| Action | Dose counter Indicator 18c | Dose counter indicator 18b |
|---|---|---|
| 1. Open device | ☐ | 1 |
| 2. Inhale | ■ | ☐ |
| 3. Close device | ■ | ☐ |

Fig. 8

Total Cassette Counter (TCC)

From the first cassette

| Action | Window 18a |
|---|---|
| 1. Before inserting the cassette. | ☐ |
| 2. Insert a cassette. | 50 |
| 3. When seven doses are taken remove the cassette. | 50 |
| 4. Insert a new cassette. | 49 |

Fig. 9

From the fourth cassette

| Action | Window 18a |
| --- | --- |
| 1. The last dose of the fourth cassette is taken. | 46 |
| 2. Insert a new cassette. | 45 |
| 3. Change the mouthpiece. | 45 |

Fig. 10

From the forty-ninth cassette

| Action | Window 18a |
| --- | --- |
| 1. The last dose of the last but one cassette is taken. | 01 |
| 2. Insert a new cassette. | 00 |
| 3. The last dose of the last cassette is taken | 00 |
| 4. The cassette stays in the device. | 00 |

USER INTERFACE

TECHNICAL FIELD

The present invention relates to dry powder inhalers DPI and more exactly to a user interface for an optimum user-friendly usage of a dry powder inhaler operating with pre-metered doses in prefabricated sealed cassettes.

BACKGROUND

Today supply and distribution of medical powders take place in many different ways. Within health care more and more is focused on the possibility to dose and distribute powder directly to the lungs of a user by means of an inhaler to obtain an efficient, fast, and user-friendly administration of the specific medical substance.

Inhalers have been developed from being very simple to the up-to-date relatively complicated devices. For the up-to-date inhalers some form of dosing process is almost entirely used for preparing the dose to be inhaled. Most often the dosing of the amount to be inhaled takes place industrially in advance creating a dose package containing of the order 5–50 doses. The a inhaler then is loaded with such a dose package forming the source of sequential doses to be administered by the inhaler. Some of the inhalers have a powder magazine from which the powder is dosed by some device for distribution to the inspiration air.

Therefore there is a demand for an arrangement, which provides an easily operable user interface for a person utilizing a dry powder inhaler for ensuring proper dosing as well as a safe operation and handling of the medical powder to be inhaled.

SHORT DESCRIPTION OF THE INVENTION

An interface arrangement is disclosed for ensuring proper dosing as well as achieving a safe operation and handling of a dry powder inhaler (DPI) used for administration of a powder to be inhaled. The interface of the present invention primarily handles the loading of cassettes carrying pre-metered doses into the dry powder inhaler. An important characteristic is that the interface by utilizing a particular coding prevents a user from loading a cassette not containing the proper powder. Additionally the interface informs the user when the present mouthpiece, after being used for a pre-defined number of inhalation operations, ought to be exchanged for a new one The exchange is necessary in order to guarantee a high level of hygiene and to eliminate build-up of retained powder, which may affect the pre-metered dose. Additionally the interface informs a user when a present cassette has delivered its last dose and must be exchanged. Also information on the number of cassettes already utilized will control that another cassette still is permitted to be loaded. If this counter of the indicator exceeds a pre-defined number of used cassettes the inhaler is by definition worn out. A worn out dry powder inhaler has to be discarded. In that case the last cassette will not be able to be released from the inhaler device but will accompany the inhaler when it is discarded.

An interface arrangement for controlling the usage of a dry powder inhaler dosing is set forth by the independent claim 1, and further embodiments are set forth by the dependent claims 2 to 7.

DESCRIPTION OF THE DRAWINGS

The invention will be described in the form of a preferred and illustrative embodiment and by means of the attached drawings, wherein like reference numbers indicate like or corresponding elements and wherein.

DESCRIPTION OF AN ILLUSTRATIVE EMBODIMENT

The present invention discloses an arrangement for operating and servicing a dry powder inhaler (DPI) comprising a body, indicators, an exchangeable mouthpiece and an exchangeable moving cassette carrying pre-metered sealed doses of dry powder. The objectives of the present arrangements are:

Means for training the user in the art of inhaling from a DPI.

Means for loading a cassette carrying pre-metered doses into the dry powder inhaler, DPI.

Means for preventing the wrong cassette from being loaded into the DPI.

Means for exchanging a used-up cassette for a new one in the DPI.

Means for informing the user of the number of doses left in the cassette.

Means for informing the user of the remaining number of cassettes, which can be loaded in the DPI before it is worn out.

Means for informing the user when the inhaler is worn out to be discarded.

Means for informing the user when a new mouthpiece should be fitted.

Means for exchanging the mouthpiece.

Means for notifying the user when the dose administration is started, ongoing and stopped.

The illustrative dry powder inhalation device comprises a body, an exchangeable mouthpiece and an exchangeable dosing member referred to as the cassette carrying one or more pre-metered doses of dry powder.

Particularly the present invention is meant to be applied at the construction of a new continuous inhaler, i.e. an inhaler that controls the powder concentration and the time interval of the dose delivery to the user, which thereby gives a number of advantages in comparison to inhalers according to prior art, which are found on the market today.

The DPI is provided with a cover, which in the closed state protects the mouthpiece against contamination by dirt, moisture etc when the DPI is not used and during transportation. The cover also serves as a means of loading a drive spring arrangement and bringing the cassette in the right position for administering the next dose.

Figure 12:
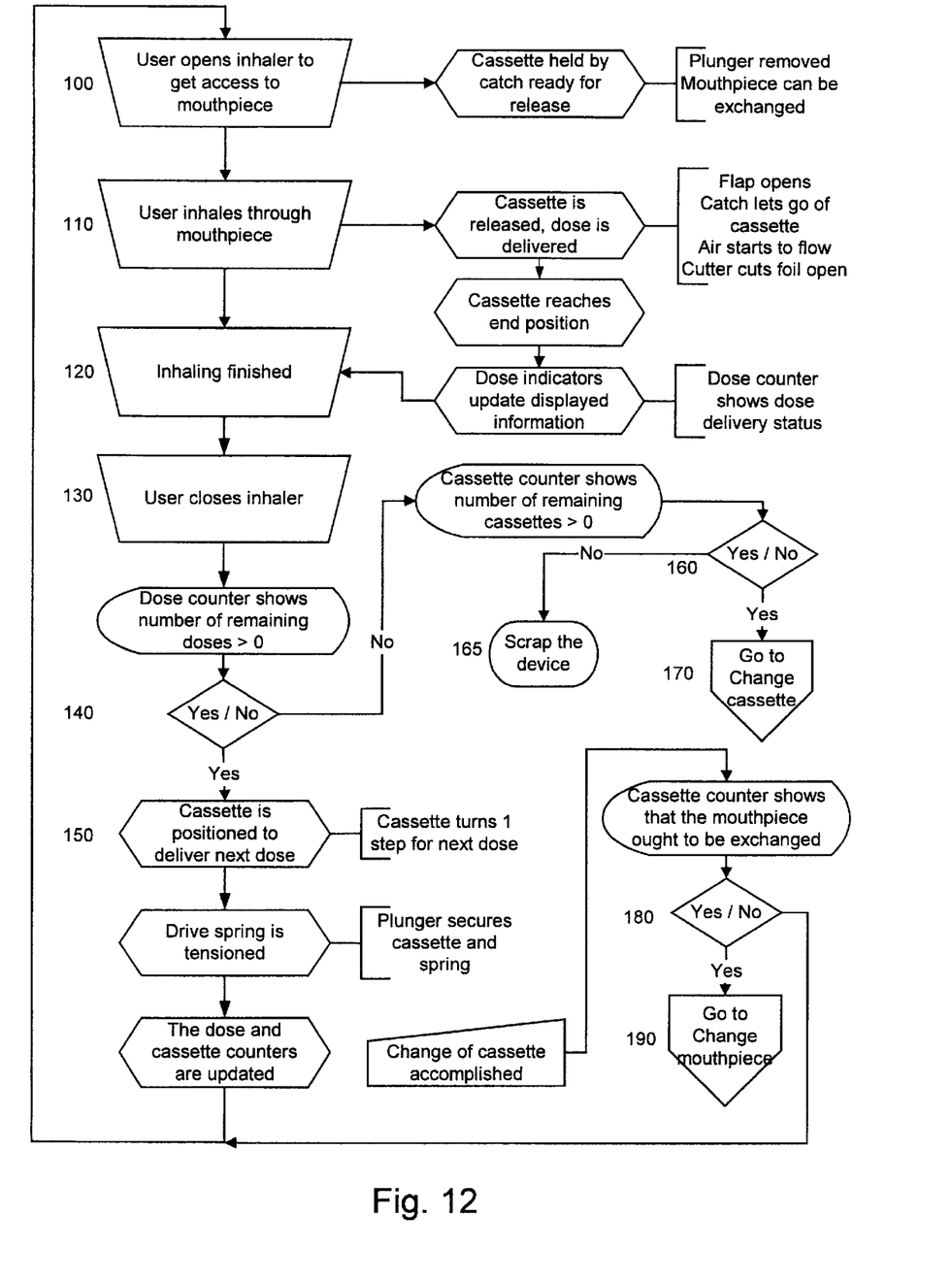
FIG. 12 illustrates a flow chart during normal operation of the operator interface of the dry powder inhaler with respect to the arrangement of a preferred embodiment of the present invention.

FIG. 12 describes the operating cycles of the DPI by illustrating the actions performed by a user and the events, which the actions give rise to in a flow chart. Taking reference in the flow chart the operation of the present invention is illustrated.

A user opens the cover to get access to the mouthpiece. When the inhalation through the suction tube in the mouthpiece begins, step 100 the cassette is released and the delivery of the dose to the airways of the user takes place, step 110. When the inhalation is finished, step 120, the user closes the cover, step 130, whereby the cassette is brought in position to deliver the next dose, step 150. When the last dose in the cassette has been administered, steps 140, 160 and 170, the user must exchange the old cassette for a new one, before the inhalation through the DPI can be repeated.

There is a dose counter indicator provided in the DPI, which will indicate when a dose has been administered, how many doses remain in the cassette, if the cassette is in the loaded position and when the cassette is used up prompting the user to exchange the old cassette for a new one.

After a set number of cassettes have been used up the user is prompted by a cassette counter indicator on the DPI to exchange the mouthpiece, steps 180 and 190. This means that a high level of hygiene is maintained throughout the lifetime of the DPI. The exchange also means that powder of the administered doses retained in the suction tube cannot accumulate to a point where it risks coming unstuck during an inhalation, giving the user too high a dose. The mouthpiece including the suction tube can easily be removed and replaced with a new one by the user.

The cassette counter indicator also indicates the number of cassettes, which remain to be loaded in the DPI before it is worn out. When the last dose in the last cassette has been administered the counter indicates that no dose remains and the cassette cannot be removed from the DPI so that the DPI including the used up last cassette must be discarded, step 160, 165, and the user must get a new DPI if further administration of powder is necessary.

Figure 1:
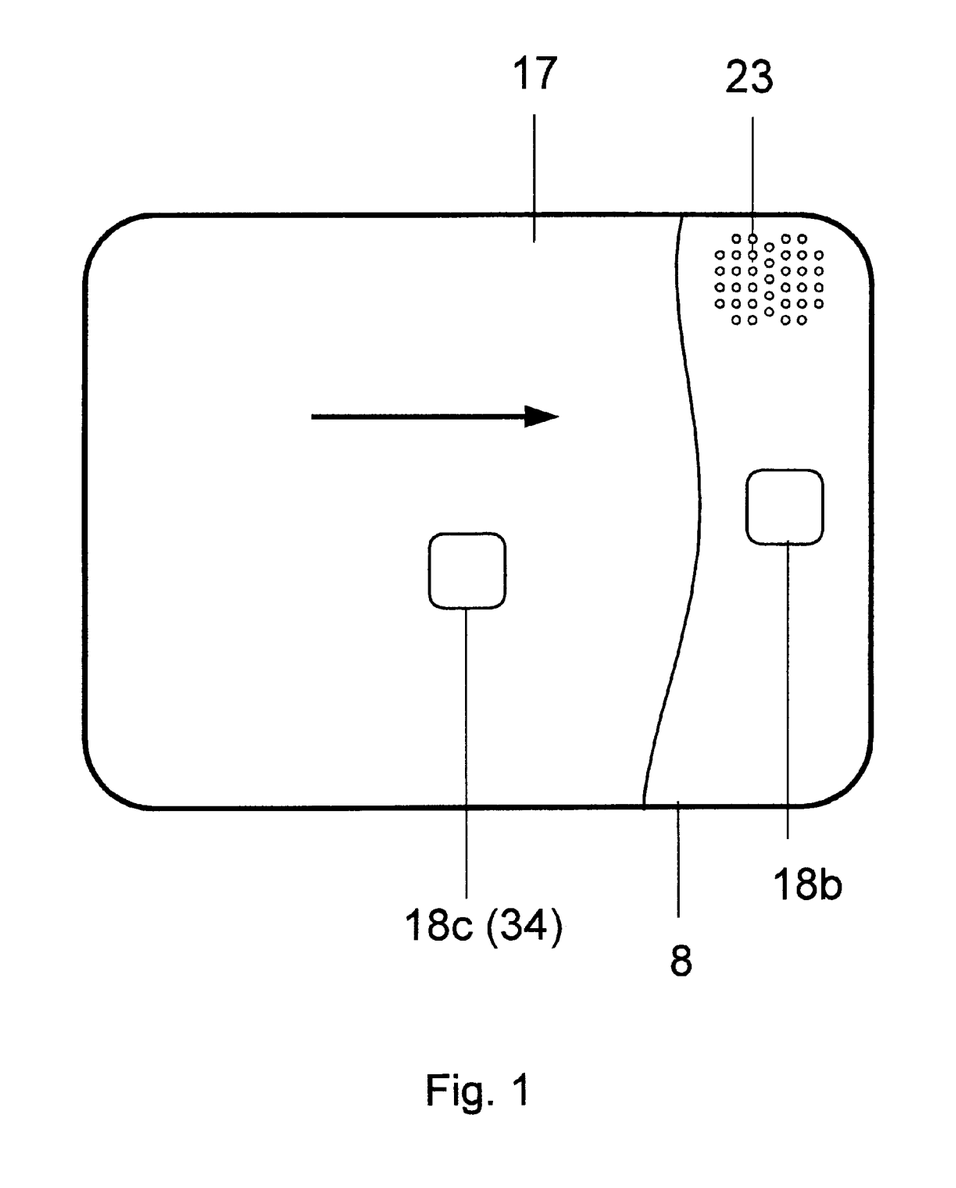
FIG. 1 illustrates a principal sketch of a front view of the inhaler in the closed state.
Figure 2:
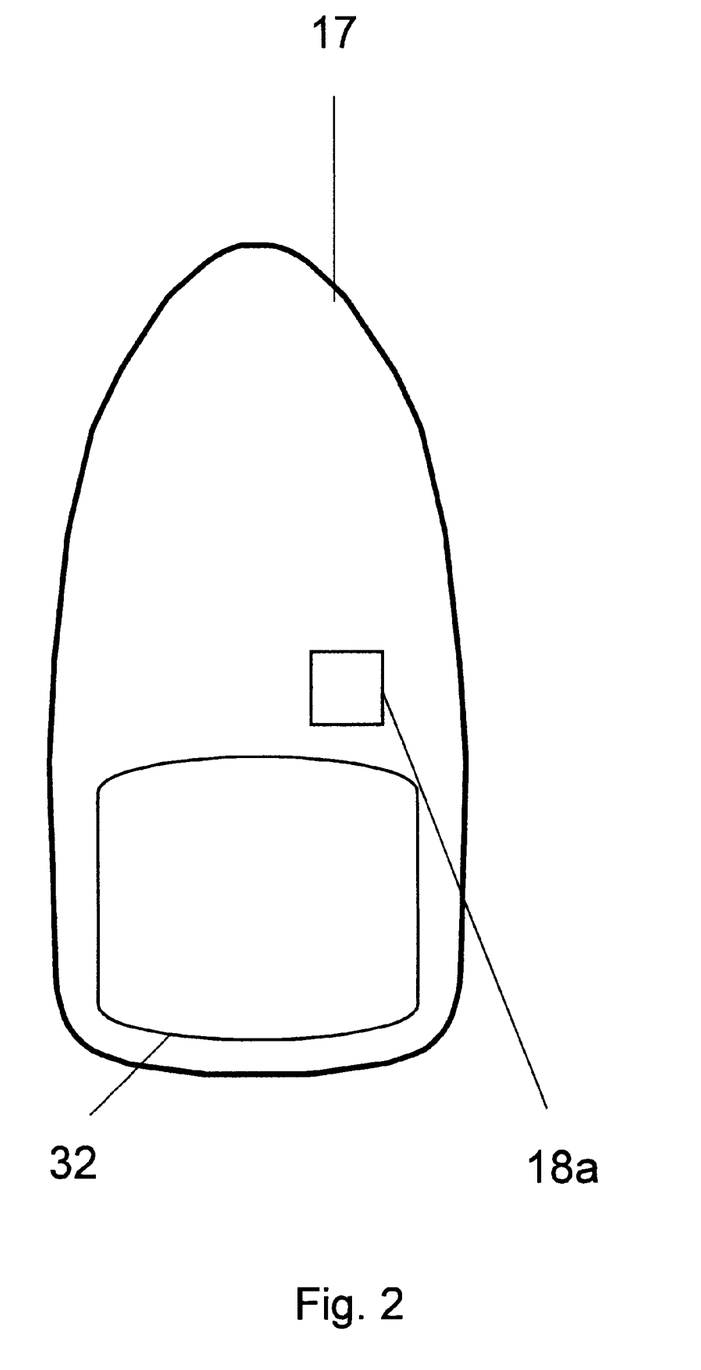
FIG. 2 illustrates a principal sketch of the left side view of the inhaler in the closed state.
Figure 3:
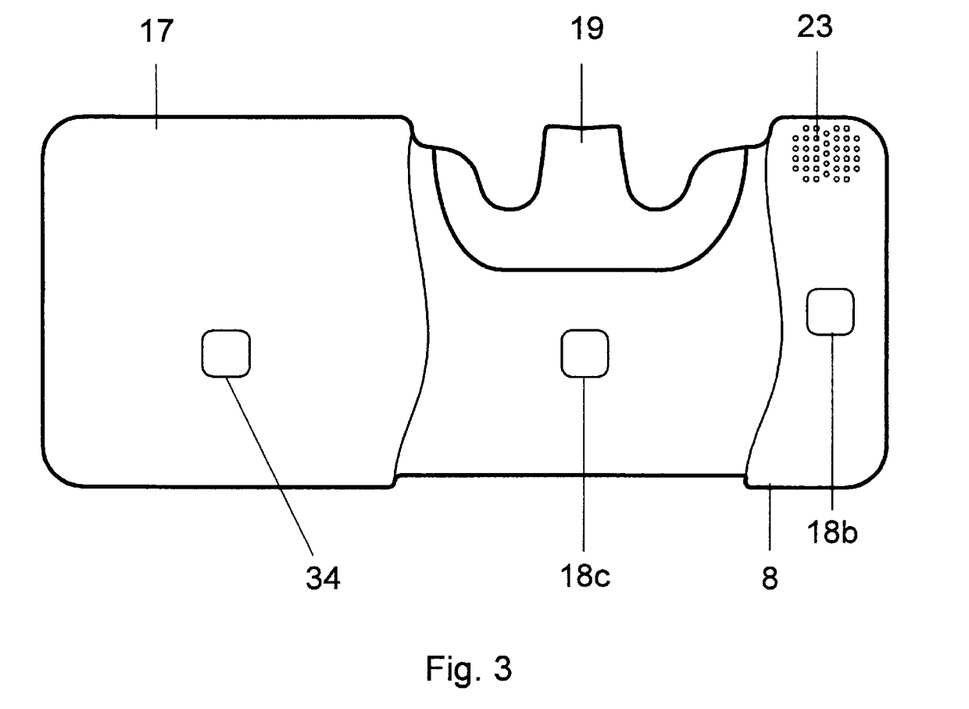
FIG. 3 illustrates a principal sketch of a front view of the inhaler in the open state.
Figure 4:
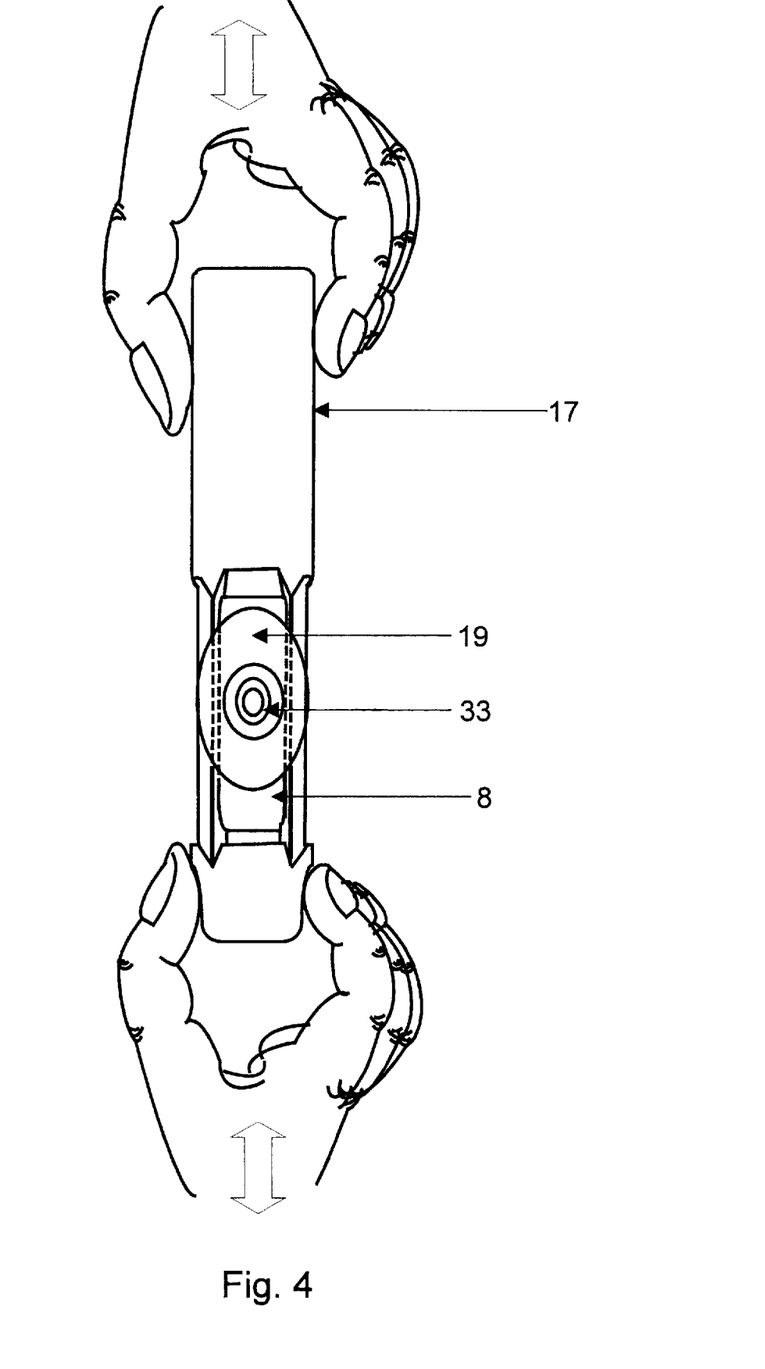
FIG. 4 illustrates the opening and closing of the dry powder inhaler.
Figure 5:
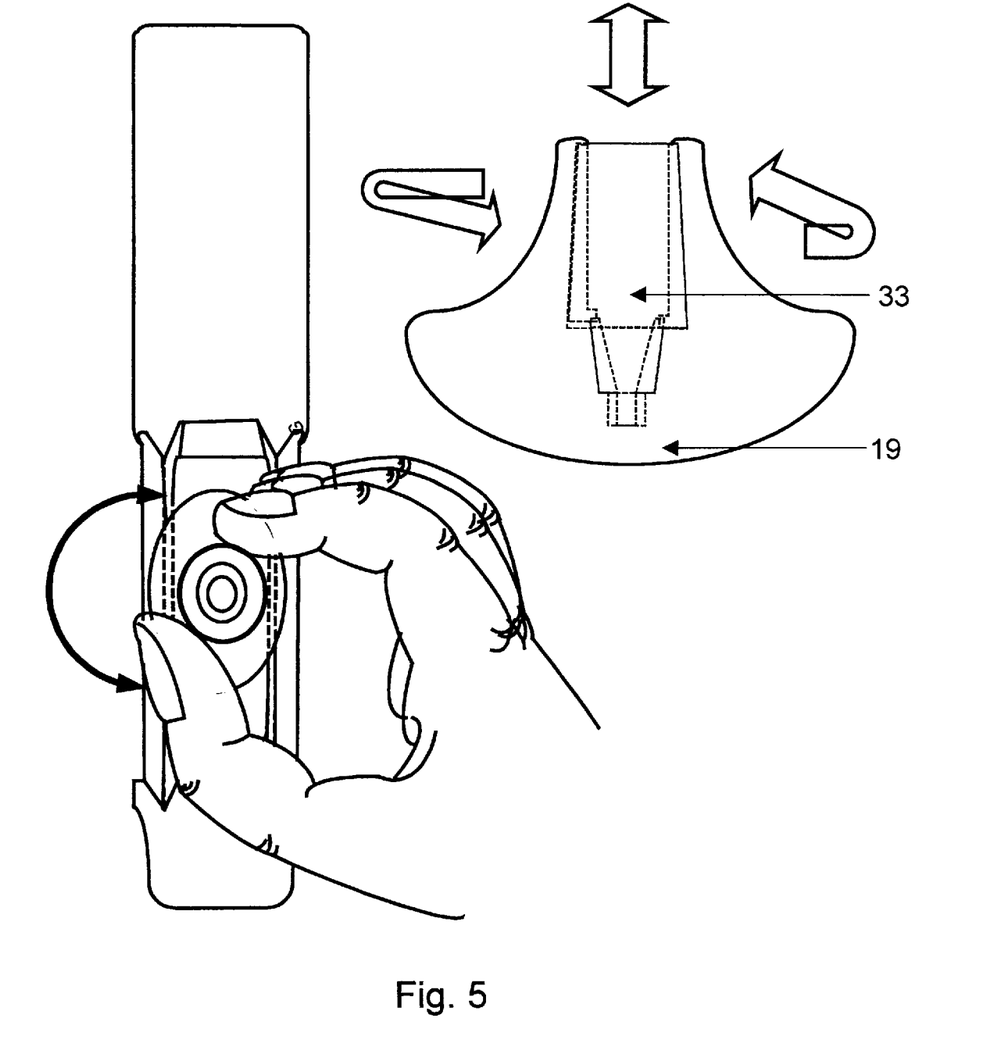
FIG. 5 illustrates exchanging the mouthpiece.

A DPI, which is utilizing the user interface of the present invention, is schematically illustrated in FIGS. 1, 2 and 3. As illustrated in FIG. 4 using one or two hands the user can pull the cover 17 to open the DPI and get access to the mouthpiece 19, which is used to inhale through the DPI. Using one or two hands the user can push the cover back in the original position to close the DPI. During storage and transportation the DPI should be in the closed state such that the cover 17 gives adequate protection of the mouthpiece 19 against ingress of dirt etc. The body 8 houses a system for triggering and controlling the administration of the doses of dry powder, normally a medical drug but other substances are also possible, from the dosing member, called cassette 4, to the user inhaling through the device.

The system for triggering and controlling the administration of the dose also causes a distinct sound to be emitted from the DPI when the inhalation triggers the administration of the dose, and a preferably different series of sounds are emitted during the dose delivery and likewise a distinct sound is emitted when the delivery has come to an end such that the user is notified that the delivery has begun, when it is ongoing and when it has come to a successful end.

Figure 6:
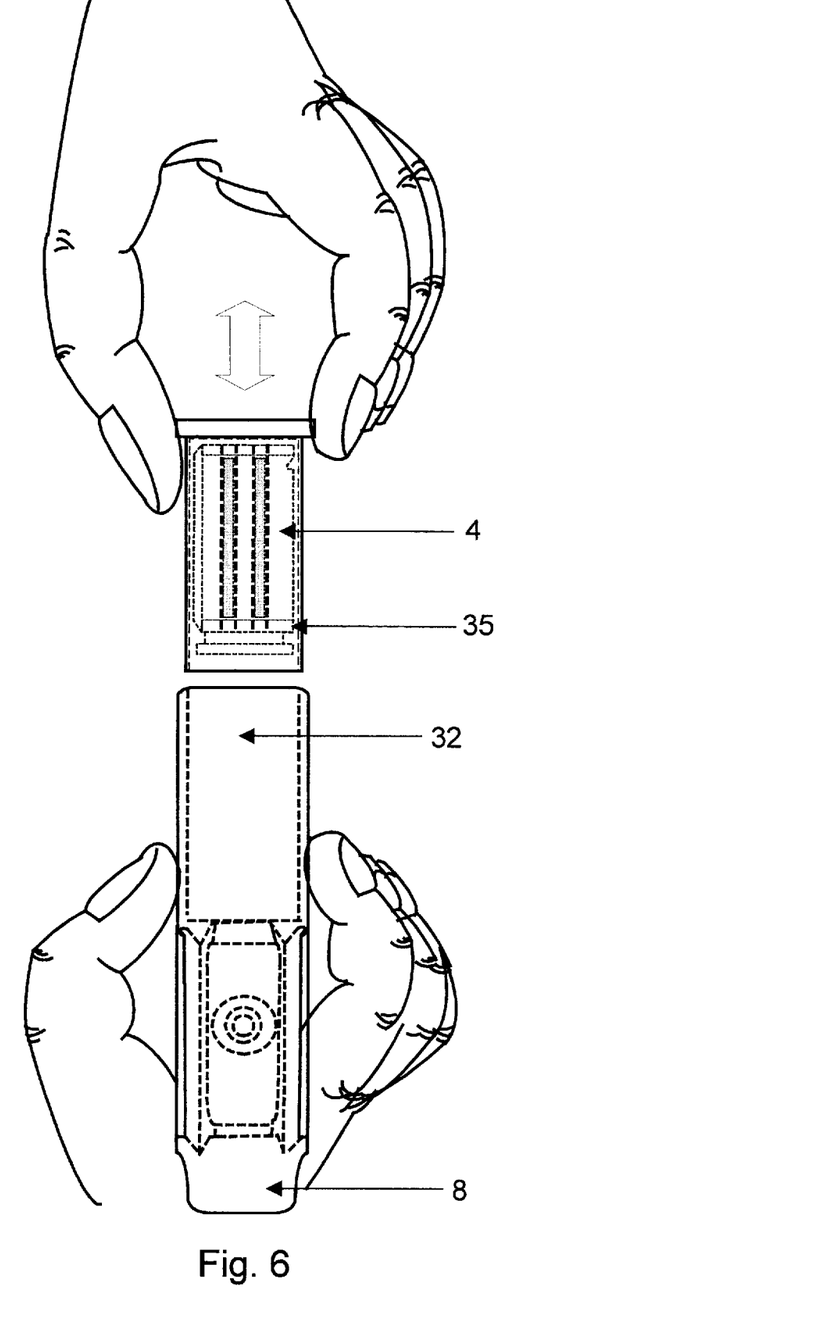
FIG. 6 illustrates exchanging the cassette.

The mouthpiece 19 comprises a suction tube 33 and a mechanism for attaching the exchangeable mouthpiece to the body 8 of the DPI. Once the user has opened the DPI he or she has easy access to the comfortably formed mouthpiece with the top end of the suction tube arranged to make the inhalation as easy as possible for the user. The material of the mouthpiece in contact with the user's mouth is preferably electrically dissipative or conductive so as to equalize any difference in the electric potential between the user and the DPI such that the delivery of the dose is not negatively affected by electrical fields resulting from unwanted potential differences. Each cassette 4 carries one or more sealed pre-metered doses of dry powder. The cassette is preferably individually packed in an airtight bag to stop moisture and other substances from contaminating the cassette. A cassette box 35 protects the cassette such that when the bag is opened and the cassette is removed the user does not come in direct contact with the cassette as illustrated in FIG. 6.

However, if the user starts with a completely new DPI the dummy cassette already in the DPI on delivery must be removed first by taking hold of the protruding dummy cassette box with the fingers and withdraw the box and cassette from the body of the DPI. If the user is unfamiliar with the DPI, the dummy cassette can be used first to practice the art of inhalation before loading the real cassette. If the user decides to practice on the dummy it is necessary to do as many practice runs, as there are doses on the standard cassette before the dummy can be removed from the DPI.

When dummy cassette and box have been removed from the DPI the user then removes the real cassette 4 with its protective box 35 from the bag. The cassette with box, illustrated in FIG. 6, are then inserted in the opening 32, intended for the purpose, in the DPI body 8, taking care that the coding of the cassette and box fit the corresponding coding of the opening. The coding is used to make it impossible to insert the wrong type of cassette in the DPI to make administration of the wrong drug impossible.

Figure 7:
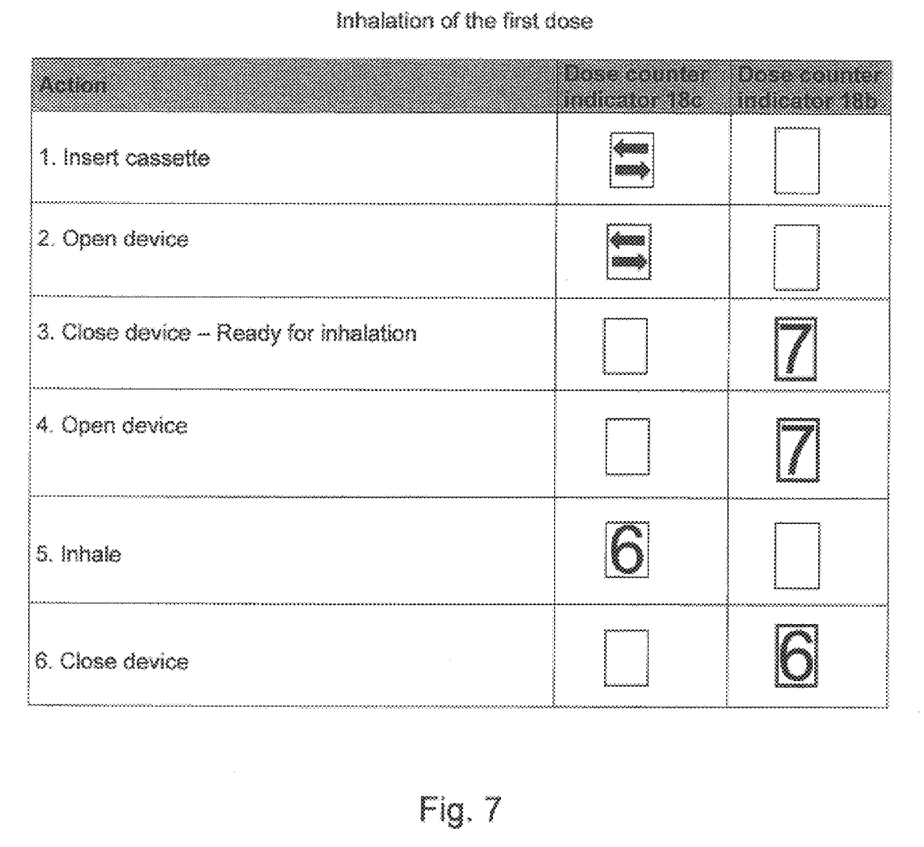
FIG. 7 illustrates the functionality of the dose counter indicator when the user utilizes the inhaler for the first time. (The example shows a cassette with a maximum of seven doses, the exact number of doses per cassette depends on the cassette and the inhaler and is particular to the application)
Figure 8:
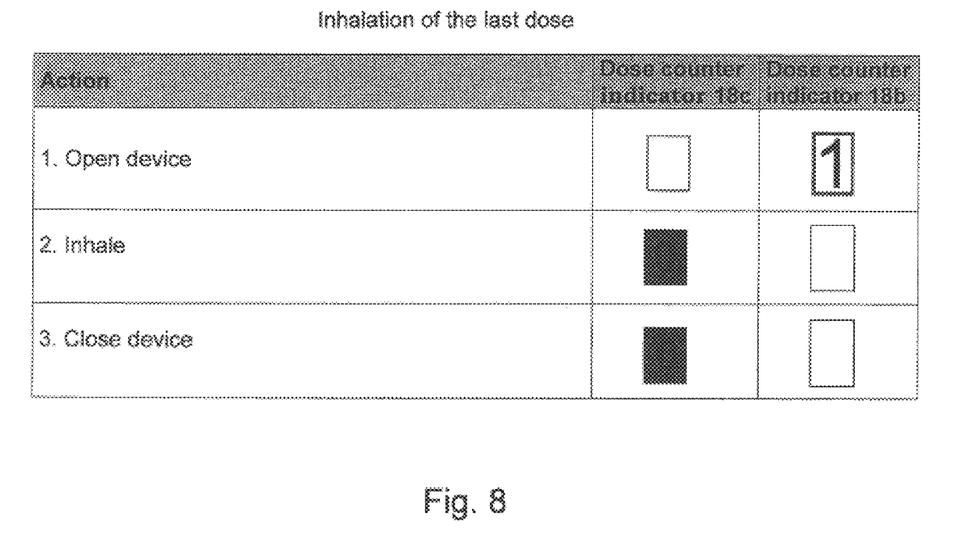
FIG. 8 illustrates the functionality of the dose counter indicator when the user inhales the last dose of a cassette.
Figure 9:
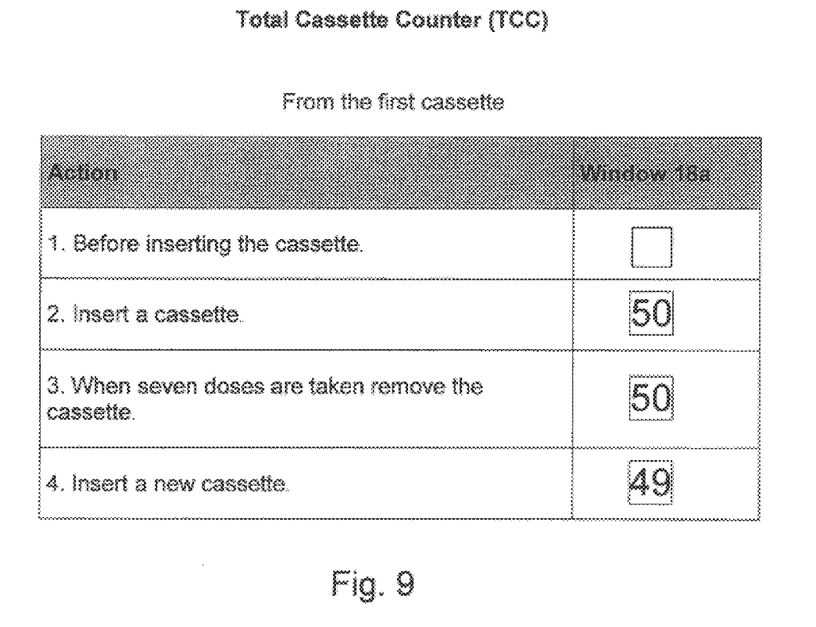
FIG. 9 illustrates the functionality of the total cassette counter (TCC), indicator starting with the first cassette. (The example shows an inhaler with 50 cassettes as the defined lifetime)
Figure 10:
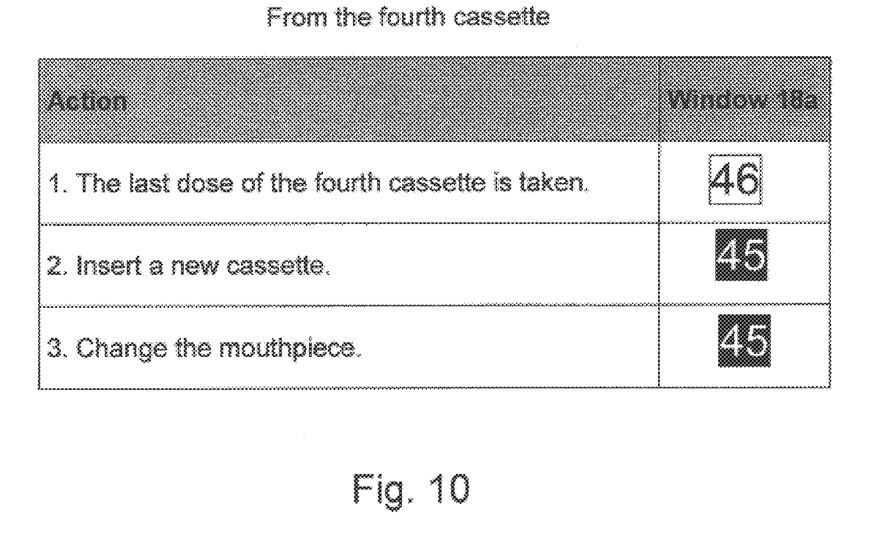
FIG. 10 illustrates the functionality of the total cassette counter indicator (TCC), every time a set number of cassettes have been used up prompting the user to exchange the mouthpiece. (The example shows an inhaler with a lifetime of 50 cassettes and a set number of 5 cassettes as the lifecycle of the mouthpieces)

Before the first dose on the cassette can be administered the dose counter indicators 18b and 18c, schematically illustrated in FIGS. 1 and 3, on the DPI prompt the user to open and then close the DPI, schematically illustrated in FIG. 4. The action can be performed by the user with one hand only if necessary, and accomplishes several things at the same time:

i The cassette is put in position to deliver the first dose ii The drive spring used to power the cassette is tightened and secured in the tightened state by a plunger element, so that it cannot unleash accidentally and drive the cassette forward   iii The dose counter 18b indicates that the first dose on the cassette is ready to be administered, schematically illustrated in FIG. 7.

iv The cassette counter counts one step down

The user can see the dose counters 18c and 18b, counting one step down for each administered dose. The dose counter 18c, directly visible when the DPI is open and indirectly through a clear window 34, if provided, when the DPI is closed, indicates when the last dose of the cassette has been administered. In cases where the window 34 is not provided, the user can still see the status of the DPI on indicator 18b. At this point the revolver mechanism locks the cassette in the box, the box is released from the DPI body and the user can remove the old box with the now empty cassette, and replace it with a new one, schematically illustrated in FIG. 6.

Figure 11:
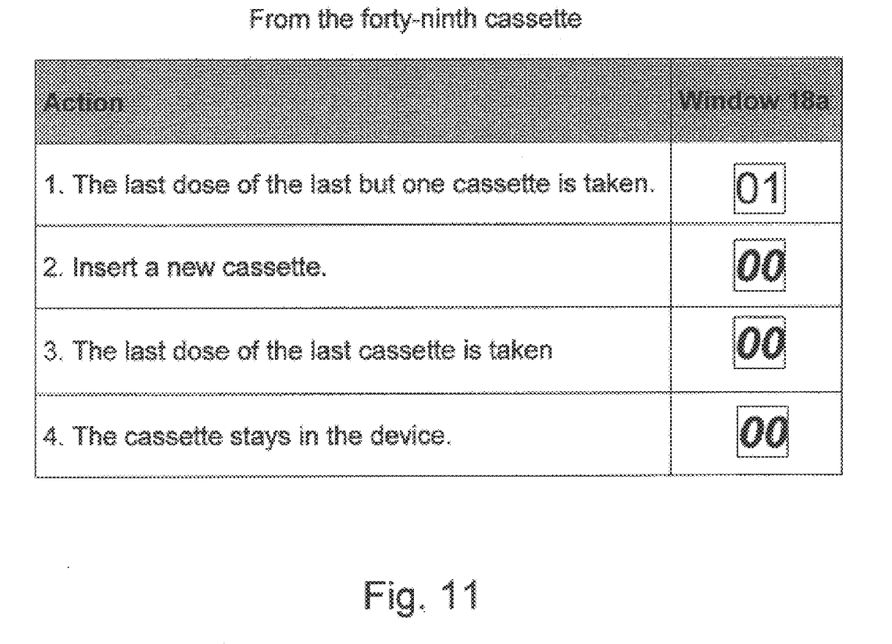
FIG. 11 illustrates the functionality of the total cassette counter indicator (TCC), from the last but one cassette. (The example shows an inhaler allowing a maximum of 50 cassettes)

Every time the user replaces an old cassette and box with a new one the cassette counter 18a counts down one step, and when the counter reaches the zero point, step 160, the DPI is worn out by definition. When the doses of the last cassette have been administered, FIG. 11, the cassette counter mechanism locks the cassette in the DPI so it cannot be removed from the DPI. The user is left with no option but to discard the whole inhaler including the last cassette, step 165 and to get a new inhaler if further medication is necessary.

The present arrangement for a user interface has been described by means of an illustrative dry powder inhaler for disclosing the operation of the interface, but it will be apparent to a person skilled in the art, that there may be performed numerous modifications and changes to the present arrangement without departure from the scope thereof, which is defined by the appended claims.

What is claimed is:

1. An interface arrangement for ensuring proper dosing as well as achieving a safe operation and handling of a dry powder inhaler used for administration of a powder to be inhaled, comprising:

means for loading a cassette carrying pre-metered doses into the dry powder inhaler in order to prepare for a number of sequential administrations of powder doses to the lungs of a user;

means for preventing a user from loading a cassette not containing the proper powder comprising an individual dosing cassette coding;

means for informing the user when a new mouthpiece has to be replaced after being used in a pre-defined number of inhalation operations thereby to guarantee a high level of hygiene and to eliminate build-up of possible retained powder.

2. The interface arrangement according to claim 1, further comprising:

means for informing the user of the number of doses left in a present cassette in use;

means for informing the user of the number of further cassettes which can be loaded in said dry powder inhaler before it is considered as worn out.

3. The interface arrangement according to claim 2, further comprising:

means for replacement of the cassette when a present cassette has delivered its last dose if the means for informing the user of the number of cassettes used states that another cassette is permitted to be loaded;

means for informing the user that the inhaler is considered worn out due to the number of already used cassettes whereby the present dry powder inhaler cannot be used further but has to be discarded.

4. The interface arrangement according to claim 1, further comprising:

means for replacement of a used mouthpiece with a new mouthpiece.

5. The interface arrangement according to claim 1, further comprising:

means for informing the user that the mouthpiece is due for replacement.

6. The interface arrangement according to claim 1, further comprising:

means for training the user in the art of inhaling from the dry powder inhaler when a new dry powder inhaler is taken into operation before a cassette containing pre-metered doses is installed, the means for training the user constituting a dummy cassette inserted into the dry powder inhaler upon delivery.

7. The inhaler arrangement according to claim 1, wherein a sound is emitted from said dry powder inhaler when an inhalation has triggered administration of a dose, a different series of sounds is emitted during the dose delivery and likewise a distinct sound is emitted from the inhaler when delivery has come to an end, thereby notifying the user that delivery of dose has begun, when delivery is ongoing arid when delivery has successfully been ended.

* * * * *